United States Patent [19]

Hirai et al.

[11] Patent Number: 4,871,765
[45] Date of Patent: Oct. 3, 1989

[54] AMINE DERIVATIVE AND ITS SALT AND ANTI-ULCER AGENT CONTAINING THE SAME

[75] Inventors: Shiro Hirai, Toyama; Hiroshi Hirano, Oyabe; Hirotoshi Arai, Toyama; Hisanari Shibata, Toyama; Yoshikazu Kusayanagi, Toyama; Kazuhiko Hashiba, Higashitonami, all of Japan

[73] Assignee: Toyama Chemical Co., Ltd., Tokyo, Japan

[21] Appl. No.: 236,726

[22] Filed: Aug. 26, 1988

[30] Foreign Application Priority Data

Aug. 28, 1987 [JP] Japan .................. 62-214292

[51] Int. Cl.$^4$ ............... A61K 31/34; C07D 307/52
[52] U.S. Cl. ................... 514/471; 549/495
[58] Field of Search .................. 549/495; 514/471

[56] References Cited

U.S. PATENT DOCUMENTS

| | | | |
|---|---|---|---|
| 4,233,302 | 11/1980 | Martin-Smith et al. | 549/60 X |
| 4,279,819 | 7/1981 | Price et al. | 549/495 X |
| 4,279,911 | 7/1981 | Martin-Smith et al. | 549/60 X |
| 4,304,780 | 12/1981 | Martin-Smith et al. | 549/60 X |
| 4,515,806 | 5/1985 | Ges et al. | 549/495 X |
| 4,643,849 | 2/1987 | Hirai et al. | 540/955 |

FOREIGN PATENT DOCUMENTS

| | | |
|---|---|---|
| 53-149936 | 12/1978 | Japan . |
| 54-109963 | 8/1979 | Japan . |
| 1604674 | 12/1981 | United Kingdom . |
| 1604675 | 12/1981 | United Kingdom . |
| 2131428 | 6/1984 | United Kingdom . |

OTHER PUBLICATIONS

Hirai et al., Chemical Abstracts, vol. 101 (1984) 191677n.

*Primary Examiner*—Richard L. Raymond
*Attorney, Agent, or Firm*—Oblon, Spivak, McClelland, Maier & Neustadt

[57] ABSTRACT

This invention relates to a novel compound represented by the formula:

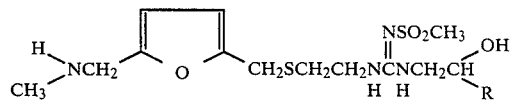

wherein R is a 4-hydroxyphenyl group, a 4-carbamoylphenyl group or a 3-methanesulfonylaminophenyl group and its salt, which have an excellent anti-ulcer effect and good stability, to a process for producing the same, and to an anti-ulcer agent containing the same.

12 Claims, No Drawings

AMINE DERIVATIVE AND ITS SALT AND ANTI-ULCER AGENT CONTAINING THE SAME

This invention relates to a novel amine derivative, a salt thereof, a process for producing the same and an anti-ulcer agent containing the same.

As a result of a study made on the basis of the fact that compounds having a histamine $H_2$-blocking activity are useful for the treatment of peptic ulcer, the present inventors had previously found novel amine derivatives which are competitively antagonistic to histamine at histamine $H_2$ receptor, and had filed applications for patent [Japanese Patent Application Kokai (Laid-Open) Nos. 88,458/84 and 97,958/85].

However, the compounds specifically illustrated in the above patent applications are not fully satisfactory in anti-ulcer effect and stability. Therefore, there has been desired a compound having a better antiulcer effect and good stability.

The present inventors have made a further study to solve the above problem and have, as a result, found that the novel compound represented by the formula [I] and its salt described below have an outstanding anti-ulcer effect, low toxicity and good stability as compared with the compounds specifically illustrated in the above patent applications. This invention has been completed based on this finding.

An object of this invention is to provide a novel amine derivative and its salt.

Another object of this invention is to provide a novel amine derivative and its salt which have an anti-ulcer activity.

A further object of this invention is to provide a process for producing a novel amine derivative or its salt.

A still further object of this invention is to provide a pharmaceutical composition containing a novel amine derivative or its salt as an active ingredient.

A still further object of this invention is to provide a method for treating peptic ulcer.

Other objects and advantages of this invention will become apparent from the following description.

According to this invention, there is provided an amine derivative represented by the formula [I]:

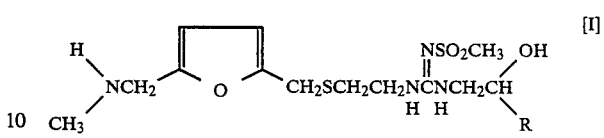

wherein R is a 4-hydroxyphenyl group, a 4-carbamoylphenyl group or a 3-methanesulfonylaminophenyl group, or its salt.

This invention further provides a process for producing the above amine derivative or its salt, as well as an anti-ulceragent containing said amine derivative or its salt.

As the salts of the amine derivative represented by the formula [I], there can be mentioned, for example, salts with inorganic acids such as hydrochloric acid, hydrobromic acid, phosphoric acid and the like; salts with organic acids such as acetic acid, propionic acid, oxalic acid, citric acid, lactic acid, maleic acid, succinic acid, tartaric acid, mandelic acid, p-toluenesulfonic acid, sulfamic acid and the like; and salts with alkali metals such as sodium, potassium and the like.

The amine derivatives of the formula [I] and their salts according to this invention include their isomers such as geometrical isomers, tautomers, optical isomers, racemic isomers and the like and also include all of their crystal forms and hydrates.

The preferable compound among the above-mentioned amine derivatives of the formula [I] and their salts of this invention is, for example, the compound in which R is a 4-hydroxyphenyl group.

The process for producing a compound of this invention is described below.

The compound of this invention can be produced according to, for example, the following production processes:

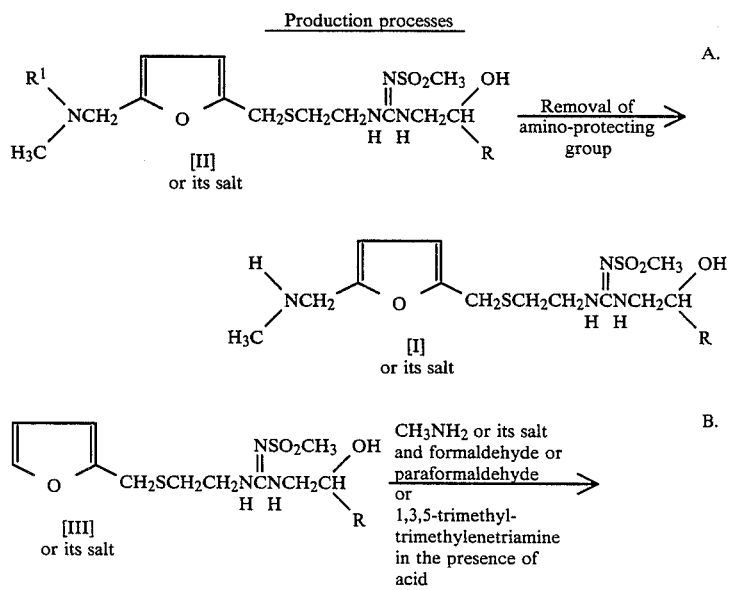

Production processes

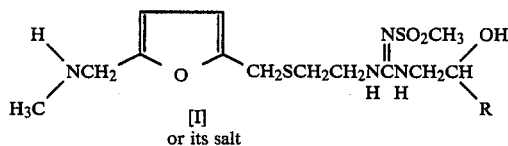

[I]
or its salt

In the above formulas, R[1] is an amino-protecting group; and R has the same meaning as defined above.

As the salts of the compounds of the formulas [II] and [III], there can be mentioned salts similar to those mentioned with respect to the compound of the formula [I]. As R[1] which is an amino-protecting group, there can be mentioned,, for example, those described in T. W. Green, "Protective Groups in Organic Synthesis" published by John Wiley & Sons, Inc. in 1981.

The above processes for producing the compound of this invention are described in detail below.

(1) Production process A

The compound of the formula [II] or its salt is subjected to removal of amino-protecting group, whereby the compound of the formula [I] or its salt can be produced.

This reaction can be specifically effected according to, for example, the method described in T. W. Green, "Protective Groups in Organic Synthesis" published by John Wiley & Sons, Inc. in 1981 or its modified method.

(2) Production process B (i) The compound of the formula [III] or its salt is reacted with methylamine or its salt and formaldehyde or paraformaldehyde, whereby the compound of the formula [I] or its salt can be produced.

The solvent used in this reaction can be any solvent as long as it does not adversely affect the reaction. As such a solvent, there can be mentioned, for example, hydrocarbons such as n-hexane, benzene, toluene, xylene and the like; halogenated hydrocarbons such as methylene chloride, chloroform and the like; nitriles such as acetonitrile and the like; esters such as ethyl acetate and the like; alcohols such as methanol, ethanol, 2-propanol and the like; ethers such as diethyl ether, tetrahydrofuran, dioxane, anisole and the like; carboxylic acids such as acetic acid and the like; etc. These solvents can be used alone or in admixture of two or more.

As the salt of methylamine, there can be mentioned, for example, salts with a mineral acid such as hydrochloric acid, hydrobromic acid, sulfuric acid or the like.

The amount of methylamine or its salt used and the amount of formaldehyde or paraformaldehyde used are each at least equimolar to the amount of the compound of the formula [III] or its salt.

Although the reaction temperature and the reaction time are not critical and may properly be varied depending on the reactants and the like, the above reaction can be effected at 10° to 150° C. for 10 minutes to 48 hours.

(ii) The compound of the formula [I] or its salt can also be produced by reacting the compound of the formula [III] or its salt with 1,3,5-trimethyltrimethylenetriamine in the presence of an acid.

The solvent used in this reaction can be any solvent as long as it does not adversely affect the reaction. As such a solvent, there can be used, for example, hydrocarbons such as n-hexane, benzene, toluene and the like; halogenated hydrocarbons such as methylene chloride, chloroform and the like; nitriles such as acetonitrile and the like; esters such as ethyl acetate and the like; alcohols such as methanol, ethanol, 2-propanol and the like; ethers such as diethyl ether, tetrahydrofuran, dioxane and the like; etc. These solvents can be used alone or in admixture of two or more.

As the acid used in the above reaction, there can be mentioned a mineral acid such as hydrogen chloride, hydrogen bromide or the like or an organic acid such as a sulfonic acid e.g. methanesulfonic acid, benzenesulfonic acid or p-toluenesulfonic acid; or the like.

The amount of 1,3,5-trimethyl-trimethylenetriamine used and the amount of the acid used are at least equimolar and at least three-fold moles, respectively, relative to the amount of the compound of the formula [III] or its salt.

Although the reaction temperature and the reaction time are not critical and may properly be varied depending on the reactants and the like, the above reaction can be effected at 10° to 150° C. for 10 minutes to 48 hours.

The amine derivative of the formula [I] or its salt thus obtained can be easily isolated and collected according to an ordinary procedure such as recrystallization, concentration, extraction, optical resolution, column chromatography or the like.

The salt of the amine derivative of the formula [I] can be easily obtained from the amine derivative in the free state according to an ordinary method.

The process for producing a compound of the formula [II] or its salt and a compound of the formula [III] or its salt as a starting material of the compound of this invention is described below.

The compound of the formula [II] or its salt and a compound of the formula [III] or its salt can be produced according to, for example, the following production processes.

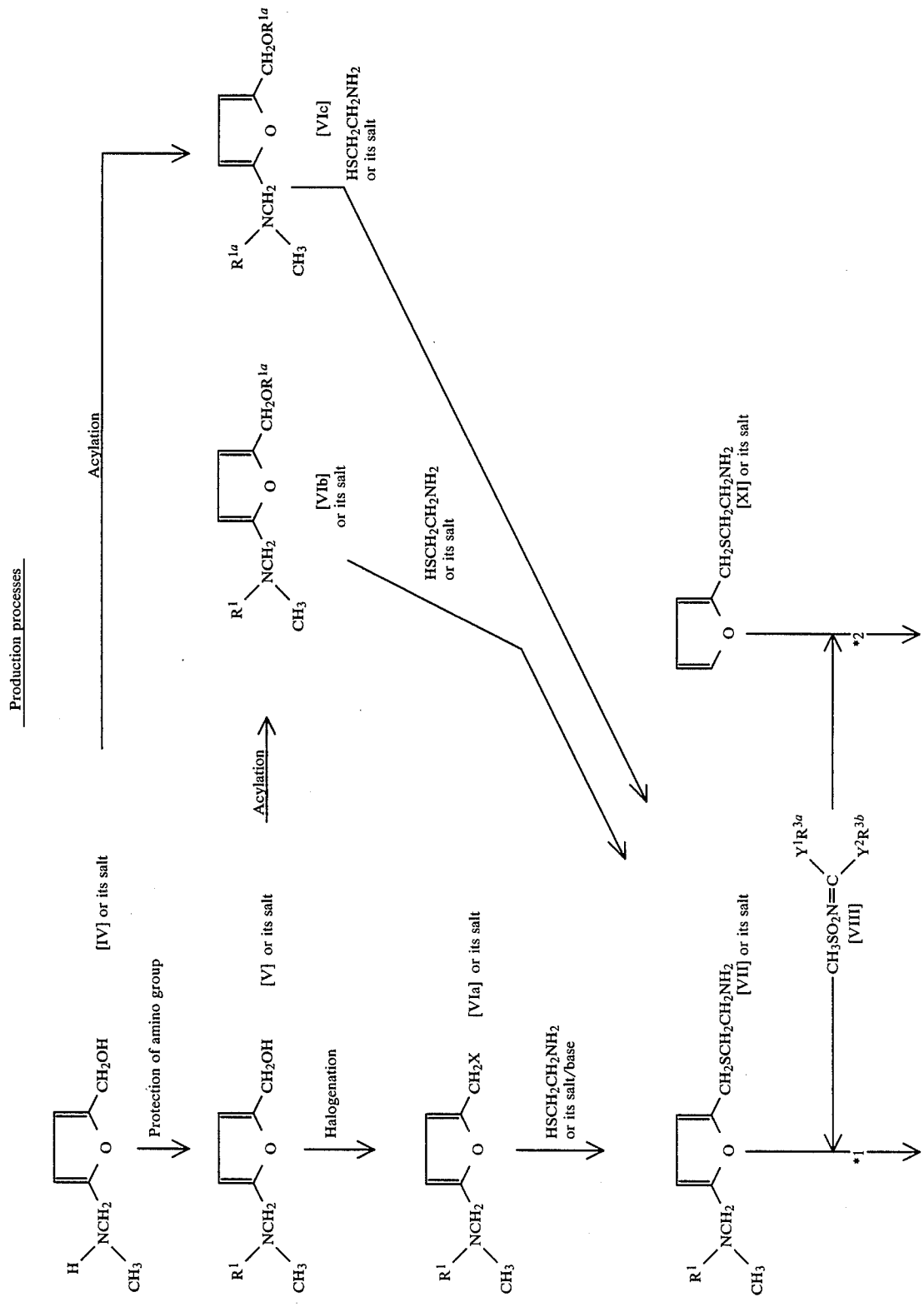

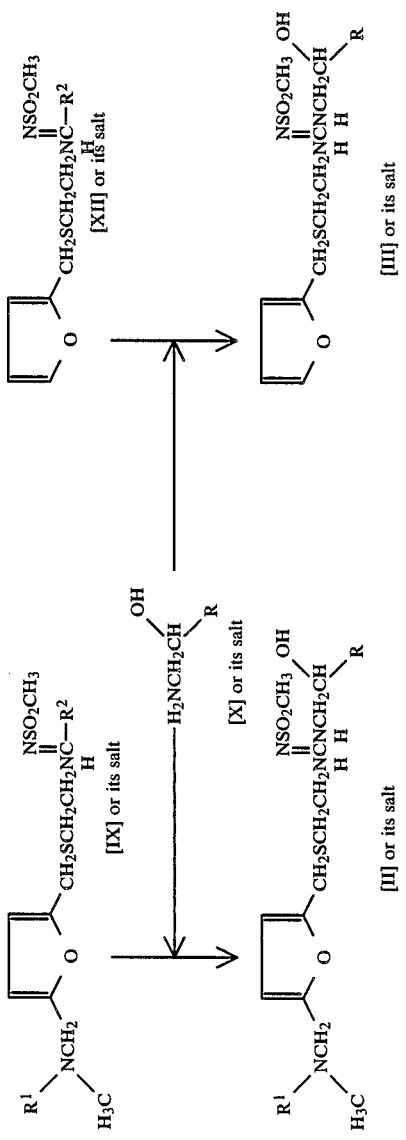

In the above formulas, $R^{1a}$ is an acyl group; $R^2$ is a removable group; $R^{3a}$ and $R^{3b}$, which may be the same or different, are substituted or unsubstituted alkyl or aryl groups, and $R^{3a}$ and $R^{3b}$ may be combined with each other to form o-phenylene or o-naphthylene group; X is a halogen atom; $Y^1$ and $Y^2$, which may be the same or different, are

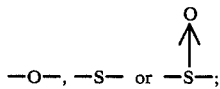

and R and $R^1$ have the same meanings as defined above.

As the salt of the compound of the formula [IV], [V], [VIa], [VIb], [VII], [IX], [X], [XI] or [XII], there can be mentioned salts similar to those mentioned with respect to the compound of the formula [I].

As $R^{1a}$ which is an acyl group, there can be mentioned, for example, $C_{1-4}$alkanoyl groups which may be substituted with halogen atoms, such as formyl, acetyl, chloroacetyl, dichloroacetyl, trichloroacetyl and the like, as well as aroyl groups such as benzoyl and the like.

As $R^2$ which is a removable group, there can be mentioned $C_{1-4}$alkoxy groups such as methoxy, ethoxy and the like; $C_{1-4}$alkylthio groups such as methylthio, ethylthio and the like; aryloxy groups such as phenoxy, naphthoxy, o-hydroxyphenoxy, o-hydroxynaphthoxy and the like; arylthio groups such as phenylthio, naphthylthio, o-mercaptophenylthio, o-mercaptonaphthylthio and the like; $C_{1-4}$alkylsulfinyl groups such as methanesulfinyl, ethanesulfinyl and the like; arylsulfinyl groups such as benzenesulfinyl, naphthalenesulfinyl and the like; etc. $R^2$ may have at least one substituent selected from halogen atoms such as fluorine, chlorine, bromine and iodine; a nitro group; a cyano group; $C_{1-4}$alkyl groups such as methyl, ethyl and the like; $C_{1-4}$alkoxy groups such as methoxy, ethoxy and the like; etc.

As the alkyl groups for $R^{3a}$ or $R^{3b}$, there can be mentioned, for example, $C_{1-4}$alkyl groups such as methyl, ethyl and the like; and as aryl groups, there can be mentioned, for example, phenyl and naphthyl. Further, $R^{3a}$ and $R^{3b}$ and the o-phenylene or o-naphthylene which $R^{3a}$ and $R^{3b}$ form when taken together may have at least one substituent same as that mentioned with respect to $R^2$.

According to the above production processes, the process for producing a compound of the formula [II] or its salt and a compound of the formula [III] or its salt for a starting material of the compound of this invention is described in detail below.

(1) The compound of the formula [IV] or its salt is subjected to amino group protection by an amino-protecting group according to an ordinarily known method, whereby the compound of the formula [V] or its salt can be produced.

(2) The compound of the formula [V] or its salt is halogenated, whereby the compound of the formula [VIa] or its salt can be produced.

This halogenation can be effected according to, for example, the methods described in Acta. Chimi. Acad. Sci. Hung., 29(1), 91–98 (1961), Tetrahedron Lett., 4, 339 (1979), J. Org. Chem. 36, 3044 (1971), or their modified methods.

(3) The compound of the formula [V] or its salt is subjected to an ordinary acylation reaction using about an equimolar amount of an acylating agent, whereby the compound of the formula [VIb] or its salt can be produced.

(4) The compound of the formula [IV] or its salt is subjected to an ordinary acylation reaction using at least two-fold equivalents of an acylating agent, whereby the compound of the formula [VIc] can be produced.

The thus obtained compounds of the formulas [VIa] and [VIb] and their salts and compounds of the formula [VIc] (these compounds are hereinafter referred to generically as the compound of the formula [VI]) can be used in the subsequent reactions without being isolated.

(5) The compound of the formula [VI] is reacted with 2-aminoethanethiol or its salt in the presence or absence of a base, whereby the compound of the formula [VII] or its salt can be produced.

The solvent used in this reaction can be any solvent as long as it does not adversely affect the reaction. As such a solvent, there can be mentioned, for example, halogenated hydrocarbons such as methylene chloride, chloroform and the like; nitriles such as acetonitrile and the like; ethers such as tetrahydrofuran, dioxane and the like; alcohols such as methanol, ethanol and the like; amides such as N,N-dimethylformamide and the like; carboxylic acid such as acetic acid and the like; water; etc. These solvents can be used alone or in admixture of two or more.

As the base, in the presence of which the reaction is effected, there can be mentioned, for example, sodium methoxide, potassium t-butoxide, sodium hydroxide, potassium hydroxide, triethylamine, and 1,8-diazabicyclo[5.4.0]-undec-7-ene (DBU).

The amount of 2-aminoethanethiol or its salt used and the amount of the base used can be each at least equimolar to the amount of the compound of the formula [VI].

Although the reaction temperature and the reaction time are not critical and may properly be varied depending on the reactants and the like, the above reaction can be effected at $-20°$ to $100°$ C. for 1 minute to 12 hours.

(6) The compound of the formula [VII] or its salt, or the compound of the formula [XI] or its salt is reacted with the compound of the formula [VIII], whereby the compound of the formula [IX] or its salt or the compound of the formula [XII] or its salt can be produced, respectively.

The solvent used in this reaction can be any solvent as long as it does not adversely affect the reaction. As such a solvent, there can be mentioned, for example, aromatic hydrocarbons such as benzene, toluene, xylene and the like; halogenated hydrocarbons such as methylene chloride, chloroform and the like; nitriles such as acetonitrile and the like; ethers such as anisole and the like; esters such as ethyl acetate; amides such as N,N-dimethylformamide and the like; alcohols such as methanol, ethanol, 2-propanol and the like; etc. These solvents can be used alone or in admixture of two or more.

The amount of the compound of the formula [VIII] used is at least equimolar to the amount of the compound of the formula [VII] or its salt or the compound of the formula [XI] or its salt.

As the preferable compound of the formula [VIII], there can be mentioned, for example, dimethyl methanesulfonylimidodithiocarbonate, diphenyl methanesulfonylimidocarbonate, 2-methanesulfonylimino-1,3-benzodioxole and the like.

Although the reaction temperature and the reaction time are not critical and may properly be varied depending on the reactants and the like, the above reaction can be effected at −10° to 150° C. for 1 minute to 24 hours.

The compound of the formula [IX] or its salt or the compound of the formula [XII] or its salt can be used in the subsequent reaction without being isolated.

(7) The compound of the formula [IX] or its salt or the compound of the formula [XII] or its salt is reacted with the compound of the formula [X] or its salt in the presence or absence of a base, whereby the compound of the formula [II] or its salt or the compound of the formula [III] or its salt can be produced, respectively.

The solvent used in this reaction can be any solvent as long as it does not adversely affect the reaction. As such a solvent, there can be mentioned, for example, aromatic hydrocarbons such as benzene, toluene, xylene and the like; halogenated hydrocarbons such as methylene chloride, chloroform and the like; nitriles such as acetonitrile and the like; ethers such as anisole and the like; esters such as ethyl acetate and the like; amides such as N,N-dimethylformamide, N,N-dimethylacetamide and the like; sulfoxides such as dimethyl sulfoxide and the like; alcohols such as methanol, ethanol, 2-propanol and the like; etc. These solvents can be used alone or in admixture of two or more.

As the base used in the above reaction, there can be mentioned, for example, inorganic bases such as sodium carbonate, potassium carbonate and the like, as well as organic bases such as potassium acetate, triethylamine, tetramethylguanidine and the like.

The amount of the formula [X] or its salt used and the amount of the base used are each at least equimolar to the amount of the compound of the formula [IX] or its salt or to the amount of the compound of the formula [XII] or its salt.

Although the reaction temperature and the reaction time are not critical and may properly be varied depending on the reactants and the like, the above reaction can be effected at 20° to 150° C. for 30 minutes to 24 hours.

The compound of the formula [II] or its salt or the compound of the formula [III] or its salt thus obtained can be easily isolated and collected according to an ordinary procedure such as recrystallization, concentration, extraction, optical resolution, column chromatography or the like.

The salt of the compound of the formula [II] or the salt of the compound of the formula [III] can be easily obtained from the compound in the free state according to an ordinary method.

The pharmacological activities of the amine derivative of the formula [I] and its salt are described below.

| Test compounds | | |
|---|---|---|
| $R^a$\NCH$_2$— (furan) —CH$_2$SCH$_2$CH$_2$NCNCH$_2$CH\R with NSO$_2$CH$_3$, OH | | |
| CH$_3$ | | |

| | No. | $R^a$ | R |
|---|---|---|---|
| | 1 | H | —C$_6$H$_4$—OH |
| Present compounds | 2 | H | —C$_6$H$_4$—NHSO$_2$CH$_3$ |
| | 3 | H | —C$_6$H$_4$—CONH$_2$ |
| Control compounds | 4 | CH$_3$ | —C$_6$H$_4$—F |
| | 5 | CH$_3$ | —C$_6$H$_4$—OH |

[I] Inhibitory activity on gastric acid secretion (pylorus ligation method)

This activity was measured in accordance with the method by H. Shay et al. described in Gastroenterology, 5, 43 (1945). Groups of six or seven Wistar rats (male, 190–230 g) were fasted for 24 hours, following which the pylorus of each rat was ligated under ether anesthesia. The test compounds were administered intraduodenally after ligation. Thereafter, the rats were subjected to celiorrhaphy and immediately 25 mg/kg of histamine was administered to them subcutaneously at the dorsal. After 3 hours, the cardia of stomach was ligated, and then the stomach was removed. The gastric juice was collected by centrifugation and the total amount was quantitated. 1 ml of the gastric juice was taken and titrated with a 0.1 N aqueous sodium hydroxide solution to an end point of pH 7.0. In administering the test compound, the compound was dissolved in dimethyl sulfoxide (DMSO) and then diluted with distilled water to obtain a 0.25% aqueous DMSO solution containing the test compound. A 0.25% aqueous DMSO solution containing no test compound was administered to control group.

The inhibition rate of gastric acid secretion was calculated from the following equation:

$$\text{Inhibition rate of gastric acid secretion (\%)} = \frac{\begin{pmatrix}\text{Acid output}\\\text{of control}\\\text{group}\end{pmatrix} - \begin{pmatrix}\text{Acid output of}\\\text{drug-treated}\\\text{group}\end{pmatrix}}{\text{Acid output of control group}} \times 100$$

Test results obtained are shown in Table 1.

TABLE 1

| No. of test compound | Dose (mg/kg) | Inhibition rate (%) |
|---|---|---|
| 1 | 0.625 | 67.6** |
|   | 1.25 | 82.2** |
| 2 | 1.25 | 51.3* |
| 3 | 1.25 | 54.2* |
| 4 | 1.25 | 30.6 |
| 5 | 5.0 | 32.7 |

Note:
**$p < 0.01$
*$p < 0.05$

[I] Acute toxicity

A test compound was administered to ICR mice (male, 27–30 g) intravenously, and the $LD_{50}$ value was calculated by the up and down method.

The results obtained are shown in Table 2.

TABLE 2

| No. of test compound | $LD_{50}$ (mg/kg) |
|---|---|
| 1 | 100.0 |
| 2 | 129.8 |
| 3 | 151.0 |
| 4 | 85.4 |
| 5 | 90.7 |

As is clear from Table 1 and Table 2, the amine derivatives of the formula [I] and their salts have an excellent inhibitory activity on gastric acid secretion and accordingly an excellent anti-ulcer activity, have a low toxicity, and therefore have a wider safety margin. Further, they have excellent stability.

The anti-ulcer agent containing the amine derivative of the formula [I] or its salt can be prepared in various forms such as tablets, hard capsules, soft capsules, granules, powders, fine granules, pills, troches, ointments, suppositories, injections, suspensions, emulsions, drops, syrups and the like according to ordinary methods. They can be administered either orally or parenterally and in particular oral administration is preferred.

In order to prepare them in various forms suitable for oral or parenteral administration, the preparation may be carried out by using pharmaceutically acceptable nontoxic additives which are ordinarily used, such as excipients, binders, lubricants, disintegrators, base for suppositories, and the like. As necessary, other additives may also be used such as isotonicity, stabilizer, dispersant, antioxidant, colorant, flavor, buffer and the like.

The above forms can comprise other drugs useful viewed from treatment purposes.

With respect to the dose and administration times of the amine derivative of the formula [I] or its salt, they can be administered orally or parenterally, generally in a dose of 1 μg/kg to 10 mg/kg a day per adult in 1 to 4 portions. Naturally, the dose and administration times may properly be varied depending on the administration route and the symptoms of patients.

This invention is explained below referring to Reference Examples, Examples and Preparation Examples, which are not by way of limitation but by way of illustration.

The mixing ratio of solvents in the Examples is by volume unless otherwise specified.

As the carrier in column chromatography, there was used a silica gel (Kieselgel 60, Art. 7734; manufactured by Merck Co.).

REFERENCE EXAMPLE 1

267 g of diphenyl carbonate and 298 g of phosphorus pentachloride were reacted at 160° C. for 15 hours with distilling off the phosphorus oxychloride generated by the reaction. After the completion of the reaction, phosphorus oxychloride and residual phosphorus pentachloride were removed by distillation under reduced pressure to obtain dichloro-diphenoxymethane. Thereto were added 600 ml of anhydrous ethyl acetate and 148 g of methanesulfonamide, and the mixture was refluxed for 8 hours. After cooling, 1 liter of n-hexane was added to the mixture and the crystals deposited were collected by filtration. The crystals were washed with water and dried to obtain 179 g (yield: 49%) of diphenyl methanesulfonylimidocarbonate having a melting point of 124°–125.5° C.

REFERENCE EXAMPLE 2

53.4 g of methanesulfonamide and 89.4 g of 2,2-dichloro-1,3-benzodioxole were heated under reflux with 400 ml of anhydrous ethyl acetate for 7 hours. After cooling, the solvent was removed by distillation under reduced pressure. To the residue thus obtained was added 200 ml of benzene, and the mixture was refluxed for 10 minutes and then cooled slowly to room temperature with stirring. The crystals deposited were collected by filtration and washed with benzene, water and 2-propanol in this order to obtain 83 g (yield: 83%) of 2-methanesulfonylimino-1,3-benzodioxole.

Melting point: 161°–163° C. (recrystallized from ethyl acetate)

REFERENCE EXAMPLE 3

(1) 23.5 g of 2,2,2-trichloroethyl chloroformate was dropwise added to 140 ml of methylene chloride solution containing 14.1 g of 5-N-methylaminomethyl-2-furanmethanol and 8.9 ml of pyridine, at 4° to 5° C. over a period of 60 minutes, and the mixture was stirred at the same temperature for 30 minutes. The reaction mixture was introduced into 100 ml of water. The organic layer was separated and dried over anhydrous magnesium sulfate. The solvent was removed by distillation under reduced pressure and the residue thus obtained was purified by a column chromatography (eluant: benzene:ethyl acetate=2:1) to obtain 16.4 g (yield: 50%) of oily 5-[N-methyl-N-(2,2,2-trichloroethoxycarbonyl)aminomethyl]-2-furanmethanol.

NMR (CDCl$_3$) δ value:
2.15 (1H, bs), 3.00 (3H, s), 4.47 (2H, s),
4.55 (2H, s), 4.76 (2H, s), 6.21 (2H, s)

(2) 7.26 g of N-chlorosuccinimide was dissolved in 100 ml of methylene chloride. Thereto was dropwise added 4.18 ml of dimethyl sulfide at 5° to 10° C. The mixture was stirred at the same temperature for 30 minutes. Thereto was dropwise added 30 ml of methylene chloride solution containing 16.4 g of 5-[N-methyl-N(2,2,2-trichloroethoxycarbonyl)aminomethyl]-2-furanmethanol, at 5° to 10° C. in 20 minutes, and stirring was effected at the same temperature for 1 hour. The reaction mixture was introduced into 100 ml of ice water. The organic layer was separated, washed with a saturated aqueous sodium chloride solution and dried over anhydrous magnesium sulfate.

Separately, 20.0 g of a 28% by weight sodium methoxide solution in methanol was dropwise added to 15 ml of a methanol solution containing 5.88 g of 2-aminoethanethiol hydrochloride with ice-cooling in a nitrogen atmosphere. Then, the dried organic layer obtained above was dropwise added thereto at 5° to 10° C. over a period of 20 minutes. The temperature of the mixture was slowly elevated to room temperature with stirring for 30 minutes. The reaction mixture was introduced into 100 ml of ice water and the organic layer was separated. Then, 70 ml of water was added to the organic layer and the mixture was adjusted to pH 1.5 with 6 N hydrochloric acid. The organic layer was separated and the solvent was removed by distillation under reduced pressure. The residue thus obtained was dissolved in 100 ml of water. The resulting aqueous solution was washed with ethyl acetate, and the aqueous layer was adjusted to pH 11 with a 5 N aqueous sodium hydroxide solution and then extracted with 150 ml of ethyl acetate. The extract was washed with a saturated aqueous sodium chloride solution and dried over anhydrous magnesium sulfate, and the solvent was removed by distillation under reduced pressure to obtain 15.6 g (yield: 80%) of oily 2-[[5-[N-methyl-N-(2,2,2-trichloroethoxycarbonyl)aminomethyl]-2-furyl]methylthio]ethylamine.

NMR (CDCl$_3$) δ value:
1.45 (2H, s), 2.45–2.95 (4H, m), 3.01 (3H, s),
3.68 (2H, s), 4.47 (2H, s), 4.77 (2H, s),
6.16 (2H, m)

(3) 13.8 g of diphenyl methanesulfonylimidocarbonate was dissolved in 50 ml of acetonitrile. With ice-cooling, thereto was added 17.7 g of 2-[[5-N-methyl-N-(2,2,2-trichloroethoxycarbonyl)aminomethyl]-2-furyl]methylthio]ethylamine, and the mixture was stirred for 10 minutes. Then, thereto were added 10.9 g of DL-octopamine, 2.3 g of potassium acetate, 10 ml of 2-propanol and 16.5 ml of triethylamine, and the mixture was refluxed for 2 hours. After cooling, 180 ml of water and 180 ml of ethyl acetate were added thereto and the organic layer was separated. The organic layer was washed with 1 N hydrochloric acid, and a saturated aqueous sodium chloride solution in this order. Then, the solvent was removed by distillation under reduced pressure. The residue thus obtained was purified by a column chromatography (eluant:benzene:ethyl acetate=1 : 3) to obtain 26.9 g (yield: 90%) of oily N-[2-hydroxy-2-(4-hydroxyphenyl)ethyl]-N'-methanesulfonyl-N''-[2-[[5-[N-methyl-N-(2,2,2-trichloroethoxycarbonyl)aminomethyl]-2-furyl]methylthio]ethyl]guanidine.

NMR (CDCl$_3$) δ value:
2.45–2.85 (2H, m), 2.84 (3H, s),
2.98 (3H, s), 3.10–3.60 (4H, m,
3.67 (2H, s), 4.43 (2H, s), 4.55–4.95 (1H, m),
4.72 (2H, s), 6.17 (2H, s), 6.77, 7.13
(4H, ABq, J=8.2 Hz).

The following compounds were obtained in a similar manner.

N-[2-(4-carbamoylphenyl)-2-hydroxyethyl]-N'-methanesulfonyl-N''-[2-[[5-[N-methyl-N-(2,2,2tri-chloroethoxycarbonyl)aminomethyl]-2-furyl]methyl-thio]ethyl]guanidine N-[2-hydroxy-2-[3-(methanesulfonylamino)phenyl]ethyl]-N'-methanesulfonyl-N''-[2-[[5-[N-methyl-N-2,2,2trichloroethoxycarbonyl)aminomethyl]-2-furyl]-methylthio]ethyl]guanidine

REFERENCE EXAMPLE 4

(1) 42.6 g of 2-methanesulfonylimino-1,3benzodioxole was suspended in 126 ml of methylene chloride. Thereto was dropwise added 31.4 g of 2-[(2furyl)methylthio]ethylamine at 10° to 15° C. Stirring was effected at the same temperature for 30 minutes. The reaction mixture was mixed with 250 ml of benzene and the resulting mixture was stirred at the same temperature for 30 minutes. The crystals deposited were collected by filtration to obtain 65.5 g (yield: 88%) of N-[2-[(2-furyl)methylthio]ethyl]-O-(2-hydroxyphenyl)-N'-methanesulfonylisourea.

Melting point: 110°–111.5° C. (recrystallized from ethyl acetate)

NMR (CDCl$_3$) δ value: 2.76 (2H, s), 2.88 (3H, s), 3.35–3.85 (2H, m), 3.75 (2H, s), 6.24 (2H, m), 6.75–7.25 (4H, m), 7.31 (1H, m)

(2) To 50 ml of acetonitrile were added 5.0 g of N-[2-[(2-furyl)methylthio]ethyl]-O-(2-hydroxyphenyl)-N'-methanesulfonylisourea, 2.9 g of DL-octopamine and 660 mg of potassium acetate. The mixture was refluxed for 50 minutes. Then, the mixture was cooled and thereafter the solvent was removed by distillation under reduced pressure. To the residue thus obtained were added 50 ml of ethyl acetate and 30 ml of water. The mixture was adjusted to pH 2.0 with 2N hydrochloric acid. The organic layer was separated, washed with a saturated aqueous sodium chloride solution and dried over anhydrous magnesium sulfate, and the solvent was removed by distillation under reduced pressure. The residue thus obtained was purified by a column chromatography (eluant: benzene:ethyl acetate=2:3) to obtain 2.8 g (yield: 51%) of N-[2-[(2-furyl)methylthio]ethyl]-N'-[2-hydroxy-2-(4-hydroxyphenyl)ethyl]-N''-methanesulfonylguanidine having a melting point of 109° to 112.5° C.

NMR (d$_6$-DMSO) δ value: 2.57 (2H, m), 2.75 (3H, s), 3.10–3.50 (4H, m), 3.80 (2H, s), 4.50–4.90 (1H, m), 6.34 (2H, s), 6.74, 7.20 (4H, ABq, J=8.3Hz), 7.55 (1H, s)

The following compounds were obtained in a similar manner.

N-[2-[(2-furyl)methylthio]ethyl]-N'-[2-hydroxy-2[3-(methanesulfonylamino)phenyl]ethyl]-N''-methanesulfonylguanidine NMR (CDCl$_3$) δ value: 2.45–2.80 (2H, m), 2.83 (3H, s), 2.93 (3H, s), 3.05–3.65 (4H, m), 3.68 (2H, s), 4.65–5.05 (1H, m), 6.21 (2H, m), 7.00–7.50 (5H, m)

N-[2-(4-carbamoylphenyl)-2-hydroxyethyl]-N'-[2[(2-furyl)methylthio]ethyl]-N''-methanesulfonylguanidine NMR (d$_6$DMSO) δ value: 2.44–2.56 (2H, m), 2.74 (3H, s), 3.10–3.50 (4H, m), 3.79 (2H, s)'4.70∝4.94 (1H, m), 6.26–6.41 (2H, m), 7.55 (1H, m), 7.44, 7.87 (4H, ABq, J=8.3Hz)

REFERENCE EXAMPLE 5

(1) 45.2 g of trichloroacetyl chloride was dropwise added to 150 ml of a methylene chloride solution containing 15.3 g of 5-N-methylaminomethyl-2-furanmethanol and 36.1 ml of triethylamine at −30° to −20° C. over a period of 1 hour. The mixture was stirred at the same temperature for 30 minutes. The reaction mixture was introduced into 100 ml of ice water. The organic layer was separated and dried over anhydrous magnesium sulfate.

The thus obtained solution was added to 28 ml of an acetic acid solution containing 18.4 g of 2-aminoethanethiol hydrochloride at room temperature. The mixture was refluxed for 5 hours. The reaction mixture was introduced into 150 ml of ice water. The resulting mixture was adjusted to pH 9.5 with a 5N aqueous sodium hydroxide solution at 5° to 10° C. The organic layer was separated, washed with a saturated aqueous sodium chloride solution and dried over anhydrous sodium sulfate. To the resulting solution was dropwise added 200 ml of an ethanol solution containing 9.72 g of anhydrous oxalic acid. Methylene chloride was removed by distillation under atmospheric pressure. The crystals deposited were collected by filtration to obtain 30.1 g (yield: 64%) of 2-[[5-[N-methyl-N(trichloroacetyl)aminomethyl]-2-furyl]methylthio]ethylamine oxalate (1:1).

Melting point: 138°–139.5° C. (recrystallized from ethanol)

NMR (d$_6$-DMSO) δ value: 2.40–3.30 (4H, m), 3.23 (3H, s), 3.81 (2H, s), 4.68 (2H, s), 6.32 (2H, s)

(2) 43.6 g of 2-[[5-[N-methyl-N-(trichloroacetyl)aminomethyl]-2-furyl]methylthio]ethylamine oxalate (1:1) was added to 180 ml of methylene chloride and 250 ml of water. 38 ml of a 5N aqueous potassium hydroxide solution was dropwise added thereto at 10° to 15° C. and dissolved. The organic layer was separated, washed with a 10% aqueous sodium chloride solution and dried over anhydrous sodium sulfate.

To the solution thus prepared was added 29.1 g of diphenyl methanesulfonylimidocarbonate with ice cooling, and the mixture was stirred for 30 minutes. Methylene chloride was removed by distillation under reduced pressure. To the residue thus obtained was added 200 ml of 2-propanol. The crystals deposited were collected by filtration to obtain 48.9 g (yield: 90%) of N-methanesulfonyl-N'-[2-[[5-[N-methyl-N(trichloroacetyl)aminomethyl]-2-furyl]methylthio]ethyl]-O-phenylisourea.

Melting point: 85°–87° C. (recrystallized from 2-propanol)

NMR (CDCl$_3$) δ value: 2.76 (2H, t, J=6.3 Hz), 2.85 (3H, s), 3.27 (3H, s), 3.40–3.75 (2H, m), 3.73 (2H, s), 4.64 (2H, s), 6.12–6.25 (2H, m), 7.00–7.41 (5H, m)

(3) To 160 ml of acetonitrile were added 32.6 g of N-methanesulfonyl-N'-[2-[[5-[N-methyl-N-(trichloroacetyl)aminomethyl]-2-furyl]methylthio]ethyl]-O-phenylisourea, 13.8 g of DL-octopamine, 21 ml of triethylamine and 2.94 g of potassium acetate. The mixture was refluxed for 1 hour in a nitrogen atmosphere. After cooling, the solvent was removed by distillation under reduced pressure. To the residue thus obtained were added 250 ml of ethyl acetate and 150 ml of water. The mixture was adjusted to pH 2.0 with 2N hydrochloric acid. The organic layer was separated, washed with a saturated aqueous sodium chloride solution and dried over anhydrous magnesium sulfate. The solvent was removed by distillation under reduced pressure. The residue thus obtained was purified by a column chromatography (eluant: benzene:ethyl acetate=1:2) to obtain 29.9 g (yield: 83%) of N-[2-hydroxy-2-(4-hydroxyphenyl)ethyl]-N'-methanesulfonyl-N"-[2-[[5-[N-methyl-N-(trichloroacetyl)aminomethyl]-2-furyl]methylthio]ethyl]guanidine.

NMR (CDCl$_3$) δ value: 2.40–2.95 (2H, m), 2.81 (3H, s), 3.05–3.80 (4H, m), 3.26 (3H, s), 3.66 (2H, s), 4.40–4.95 (1H, m), 4.60 (2H, s), 6.10–6.30 (2H, m), 6.75, 7.11 (4H, ABq, J=8.5 Hz)

REFERENCE EXAMPLE 6

(1) 11.6 g of diphenyl methanesulfonylimidocarbonate was dissolved in 40 ml of methylene chloride. With ice-cooling, thereto was added 15 g of 2-[[5-[N-methyl-N-(2,2,2-trichloroethoxycarbonyl)aminomethyl]-2furyl]methylthio]ethylamine. The mixture was stirred for 10 minutes. The solvent was removed by distillation under reduced pressure. The residue thus obtained was purified by a column chromatography (eluant: benzene:ethyl acetate=2:1) to obtain 17.8 g (yield: 78%) of oily N-methanesulfonyl-N'-[2-[[5-[N-methyl-N-(2,2,2-trichloroethoxycarbonyl)aminomethyl]-2-furyl]methylthio]ethyl]-O-phenylisourea.

NMR (CDCl$_3$) δ value: 2.77 (2H, t, J=6.4 Hz), 2.86 (3H, s), 3.00 (3H, s), 3.40–3.75 (2H, m), 3.73 (2H, s), 4.45 (2H, s), 4.77 (2H, s), 6.16 (2H, s), 7.00–7.45 (5H, m)

(2) In 11 ml of dimethyl sulfoxide was dissolved 5.4 g of N-methanesulfonyl-N'-[2-[[5-[N-methyl-N-(2,2,2trichloroethoxycarbonyl)aminomethyl]-2-furyl]methylthio] -ethyl]-O-phenylisourea. Thereto was added 2.9 g of S(+)-octopamine ([α]$_D^{25}$=+57.4° (C=1, 0.1N HCl)). The mixture was stirred in a nitrogen atmosphere at room temperature for 10 hours. 50 ml of ethyl acetate was added, and the resulting mixture was washed with 0.5N hydrochloric acid and a saturated aqueous sodium chloride solution in this order and dried over anhydrous magnesium sulfate. The solvent was removed by distillation under reduced pressure. The residue thus obtained was purified by a column chromatography (eluant: benzene:ethyl acetate=1:3) to obtain 5.2 g (yield: 86%) of oily S(+)-N-[2-hydroxy-2-(4hydroxyphenyl)ethyl]-N'-methanesulfonyl-N"-[2-[[5-[N-methyl-N-(2,2,2-trichloroethoxycarbonyl)aminomethyl]2-furyl]methylthio]ethyl]guanidine.

[α]$_D^{25}$=+6.5° (C=1, methanol)

In a similar manner and using R(-)-octopamine ([α]$_D^{25}$=−55.1° (C=1, 0.1N HCl)) in place of S(+)octopamine, there was obtained R(−)-N-[2-hydroxy-2(4-hydroxyphenyl)ethyl]-N'-methanesulfonyl-N"-[2-[[5[N-methyl-N-(2,2,2-trichloroethoxycarbonyl)aminomethyl]2-furyl]methylthio]ethyl]guanidine.

EXAMPLE 1

(1) In 370 ml of tetrahydrofuran was dissolved 26.9 g of N-[2-hydroxy-2-(4-hydroxyphenyl)ethyl]-N'-methanesulfonyl-N"-[2-[[5-[N-methyl-N-(2,2,2trichloroethoxycarbonyl)aminomethyl]-2-furyl]methylthio] -ethyl]guanidine. Thereto were added 320 ml of a 0.5 M aqueous potassium dihydrogen phosphate solution and 42 g of an active zinc powder, and the mixture was stirred at room temperature for 3 hours. The reaction mixture was adjusted to pH 9.8 with a 5N aqueous sodium hydroxide solution and extracted with 370 ml of ethyl acetate. The solvent of the extract was removed by distillation under reduced pressure. The residue thus obtained was purified by a column chromatography (eluant:chloroform:methanol:aqueous ammonia solution=85:15:1) and then recrystallized from 95% aqueous ethanol solution to obtain 12.6 g (yield: 65%) of N-[2-hydroxy-2-(4-hydroxyphenyl)ethyl]-N'-methanesulfonyl-N"-[2-[[5-(methylamino)methyl-2-furyl]methylthio]ethyl]guanidine having a melting point of 146.5° to 147° C..

IR (KBr) cm$^{-1}$: 1580, 1255, 1105

NMR (d$_6$-DMSO) δ value: 2.24 (3H, s), 2.35–2.65 (2H, m), 2.74 (3H, s), 3.00–3.50 (4H, m), 3.56 (2H, s), 3.74 (2H, s), 4.50–4.80 (1H, m), 6.15 (2H, m), 6.71, 7.18 (4H, ABq, J=8.5Hz)

The following compounds were obtained in a similar manner.

N-[2-(4-carbamoylphenyl)-2-hydroxyethyl]-N'-methanesulfonyl-N"-[2-[[5-(methylamino)methyl-2furyl]-methylthio]ethyl]guanidine NMR (d$_6$-DMSO) δ value: 2.25 (3H, s), 2.35–2.65 (2H, m), 2.74 (3H, s), 2.90–3.60 (4H, m), 3.57 (2H, s), 3.75 (2H, s), 4.65–5.00 (1H, m), 6.18 (2H, m), 7.45, 7.86 (4H, ABq, J=8.2Hz)

N-[2-hydroxy-2-[3-(methanesulfonylamino)phenyl]ethyl]-N'-methanesulfonyl-N''-[2-[[5-(methylamino)methyl-2-furyl]methylthio]ethyl]guanidine NMR (CDCl$_3$) δ value: 2.25 (3H, s), 2.55–2.85 (2H, m), 2.86 (3H, s), 2.97 (3H, s), 3.10–3.70 (4H, m), 3.61 (2H, s), 3.69 (2H, s), 4.70–5.00 (1H, m), 6.10 (2H, s), 7.00–40 (4H, m)

(2) In 1430 ml of 95% aqueous ethanol solution was dissolved 239 g of N-[2-(4-carbamoylphenyl)-2hydroxyethyl]-N'-methanesulfonyl-N''-[2-[[5-(methylamino)methyl-2-furyl]methylthio]ethyl]guanidine. Thereto was added a solution formed by dissolving 46.8 g of oxalic acid in 240 ml of 95% aqueous ethanol solution. Further, 2.5 g of a seed crystal was added thereto. The mixture was stirred at 40° C. for 3 hours and at room temperature for 3 hours and then allowed to stand overnight. The crystals deposited were collected by filtration to obtain 257 g (yield: 91%) of N-[2-(4-carbamoylphenyl)-2-hydroxyethyl]-N'-methanesulfonyl-N''[2-[[5-(methylamino)methyl-2-furyl]methylthio]ethyl]guanidine oxalate (1:1). Melting point: 142.5°–145.5° C. (recrystallized from 95% aqueous ethanol solution)

NMR (D$_2$O) δ value: 2.62 (2H, t, J=6.4Hz), 2.73 (3H, s), 2.85 (3H, s), 3.34 (2H, t, J=6.4Hz), 3.61 (2H, d, J=5.8 Hz), 3.77 (2H, s), 4.26 (2H, s), 5.05 (1H, t, J=5.8Hz), 6.34, 6.60 (2H, ABq, J=3.4 Hz), 7.54, 7.87 (4H, ABq, J=8.3 Hz)

In a similar manner and using, as a solvent, a mixture of methanol and ethanol (1:2.5) and, as an acid, 98% orthophosphoric acid, there was obtained N-[2-(4-carbamoylphenyl)-2-hydroxyethyl]-N'-methanesulfonyl-N''-[2-[[5-(methylamino)methyl-2-furyl]methylthio]ethyl]guanidine phosphate (1:1) in an yield of 95%. Melting point: 140°–142° C. [recrystallized from ethanol and acetic acid (4:1)]NMR (D20) δ value: 2.63 (2H, t), 2.71 (3H, s), 2.81 (3H, s), 3.11 (3H, s), 3.36 (2H, t), 3.58 (2H, d), 3.79 (2H, s), 4.25 (2H, s), 4.97 (1H, t), 6.35, 6.59 (2H, ABq, J=3.1Hz), 7.16–7.68 (4H, m)

In a similar manner, there was obtained amorphous N-[2-hydroxy-2-[3-(methanesulfonylamino)phenyl]ethyl]-N'-methanesulfonyl-N''-[2-[[5-(methylamino)methyl-2-furyl]methylthio]ethyl]guanidine hydrochloride.

NMR (D$_2$O) δ value: 2.63 (2H, t), 2.71 (3H, s), 2.81 (3H, s), 3.11 (3H, s), 3.36 (2H, t), 3.58 (2H, d), 3.79 (2H, s), 4.25 (2H, s), 4.97 (1H, t), 6.35, 6.59 (2H, ABq, J=3.1 Hz), 7.16–7.68 (4H, m)

EXAMPLE 2

240 mg of methylamine hydrochloride was dissolved in a 0.27 ml of 37% (w/w) aqueous formalin solution. Thereto was added, at room temperature, 2.5 ml of a tetrahydrofuran solution containing 500 mg of N-[2-[(2-furyl)methylthio]ethyl]-N'-[2-hydroxy-2(4-hydroxyphenyl)ethyl]-N''-methanesulfonylguanidine. The mixture was stirred at the same temperature for 5 hours. The reaction mixture was introduced into 30 ml of water. The resulting mixture was adjusted to pH 9.5 with a 1N aqueous sodium hydroxide solution and extracted with two 50-ml portions of a 1:1 mixture of ethyl acetate and tetrahydrofuran. The extracts were combined and dried over anhydrous magnesium sulfate and the solvent was removed by distillation under reduced pressure. The residue thus obtained was purified by a column chromatography (eluant:chloroform:methanol:aqueous ammonia solution=85:15:1) to obtain 220 mg (yield: 40%) of N-[2-hydroxy-2-(4-hydroxyphenyl)ethyl]-N'-methanesulfonyl-N''-[2-[[5-(methylamino)methyl-2-furyl]methylthio]ethyl]guanidine.

This compound showed the same melting point, IR spectrum and NMR spectrum as those of the compound obtained in Example 1.

EXAMPLE 3

To 10 ml of a tetrahydrofuran solution containing 310 mg of 1,3,5-trimethyl-trimethylenetriamine were added 1.3 g of p-toluenesulfonic acid monohydrate and 1.0 g of N-[2-[(2-furyl)methylthio]ethyl]-N'-[2-hydroxy-2-(4-hydroxyphenyl)ethyl]-N''methanesulfonylguanidine. The mixture was stirred at room temperature for 3 hours. The reaction mixture was introduced into 30 ml of water. The resulting mixture was adjusted to pH 9.5 with a 1N aqueous sodium hydroxide solution and extracted with two 50-ml portions of a 1:1 mixture of ethyl acetate and tetrahydrofuran. The extracts were combined and dried over anhydrous magnesium sulfate and the solvent was removed by distillation under reduced pressure. The residue thus obtained was purified by a column chromatography (eluant:chloroform:methanol:aqueous ammonia solution=85:15:1) to obtain 440 mg (yield: 40%) of N-[2-hydroxy-2-(4hydroxyphenyl)ethyl]-N'-methanesulfonyl-N''-[2-[[5-(methylamino)methyl-2-furyl]methylthio]ethyl]guanidine.

This compound showed the same melting point, IR spectrum and NMR spectrum as those of the compound obtained in Example 1(1).

EXAMPLE 4

9.4 g of N-[2-hydroxy-2-(4-hydroxyphenyl)ethyl]-N'-methanesulfonyl-N''-[2-[[5-[N-methyl-N(trichloroacetyl)aminomethyl]-2-furyl]methylthio]ethyl]guanidine was dissolved in a mixture of 8 ml of ethanol and 47 ml of a 1N aqueous sodium hydroxide solution in a nitrogen atmosphere. The mixture was stirred at room temperature for 2 hours. Then, the mixture was adjusted to pH 9.7 with 6N hydrochloric acid with ice-cooling, a seed crystal was added thereto and the mixture was stirred for 4 hours at room temperature. The crystals deposited were collected by filtration to obtain 6.0 g (yield: 84%) of N-[2-hydroxy-2-(4hydroxyphenyl)ethyl]-N'-methanesulfonyl-N''-[2-[[5-(methylamino)methyl-2-furyl]methylthio]ethyl]guanidine.

This compound showed the same melting point, IR spectrum and NMR spectrum as those of the compound obtained in Example 1 (1).

EXAMPLE 5

S(+)-N-[2-hydroxy-2-(4-hydroxyphenyl)ethyl]N'-methanesulfonyl-N''-[2-[[5-[N-methyl-N-(2,2,2-trichloroethoxycarbonyl)aminomethyl]-2-furyl]methylthio]ethyl]guanidine was treated in the same manner as in Example 1 (1) to obtain S(−)-N-[2-hydroxy-2-(4-hydroxyphenyl)ethyl]-N'-methanesulfonyl-N''-[2-[[5-(methylamino)methyl-2-furyl]methylthio]ethyl]guanidine.

$[\alpha]_D^{25} = -6.6°$ (C=1, 0.1N HCl)

The following compound was obtained in a similar manner:

R(+)-N-[2-hydroxy-2-(4-hydroxyphenyl)ethyl]-N'-methanesulfonyl-N''-[2-[[5-(methylamino)methyl-2furyl]methylthio]ethyl]guanidine.

$[\alpha]_D^{25} + 6.3°$ (C=1, 0.1N HCl)

EXAMPLE 6

250 mg of methylamino hydrochloride and 170 mg of 95% paraformaldehyde were added to 1.5 ml of methanol. The mixture was refluxed for 90 minutes. Thereto was added 1.5 ml of a methanol solution containing 500 mg of N-[2-[(2-furyl)methylthio]ethyl]-N'-[[2-hydroxy-2-(4-hydroxyphenyl)]ethyl]-N''-methanesulfonylguanidine at room temperature. The mixture was subjected to reaction at the same temperature for 2 days. The solvent was removed by distillation under reduced pressure. To the residue thus obtained was added 20 ml of water. The mixture was adjusted to pH 9.6 with a 5N aqueous sodium hydroxide solution and extracted with two 30-ml portions of a 1:1 mixture of ethyl acetate and tetrahydrofuran. The extract was combined and dried over anhydrous magnesium sulfate and the solvent was removed by distillation under reduced pressure. The residue thus obtained was purified by a column chromatography (eluant: chloroform:methanol:aqueous ammonia solution=85:15:1) to obtain 220 mg (yield: 40%) of N-[2-hydroxy-2-(4-hydroxyphenyl)ethyl]-N'-methanesulfonyl-N''-[2-[[5-(methylamino)methyl-2-furyl]methylthio]ethyl]guanidine.

This compound showed the same melting point, IR spectrum and NMR spectrum as those of the compound obtained in Example 1 (1).

EXAMPLE 7

(1) 5.61 g of N-[2-[(2-furyl)methylthio]ethyl]N'-[2-hydroxy-2-(4-hydroxyphenyl)ethyl]-N''-methanesulfonylguanidine and 1.75 g of 4-(N,N-dimethylamino)pyridine were dissolved in a mixture of 20 ml of methylene chloride and 5.6 ml of N,N-dimethylformamide. To this solution was dropwise added 8 ml of a methylene chloride solution containing 2.00 g of benzoyl chloride at −35° to −25° C. over a period of 30 minutes. The mixture was stirred at the same temperature for 30 minutes. The reaction mixture was washed with 30 ml of water and 30 ml of a saturated aqueous sodium chloride solution in this order and dried over anhydrous magnesium sulfate. The solvent was removed by distillation under reduced pressure. The residue thus obtained was purified by a column chromatography (eluant: benzene:ethyl acetate=1:1) to obtain 5.40 g (yield: 77%) of N-[2-(4-benzoyloxyphenyl)-2-hydroxy]ethyl-N'-[[(2-furyl)methylthio]ethyl]-N''-methanesulfonylguanidine.

NMR (CDCl$_3$) δ value: 2.69 (2H, t), 2.88 (3H, s), 3.10–3.55 (4H, m), 3.73 (2H, s), 4.90 (1H, m), 6.15–6.35 (2H, m), 7.10–7.70 (8H, m), 8.05–8.30 (2H, m)

(2) 2.11 g of methylamine hydrochloride and 1.48 g of 95% paraformaldehyde were added to 10 ml of methanol. The mixture was refluxed for 1.5 hours. After cooling, thereto was added 15 ml of a methanol solution containing 5.40 g of N-[2-(4-benzoyloxyphenyl)-2-hydroxy]-ethyl-N'-[2-[(2-furyl)methylthio]ethyl]-N''-methanesulfonylguanidine. The resulting mixture was stirred at room temperature for 24 hours. 50 ml of ethyl acetate and 50 ml of water were added thereto. The resulting mixture was adjusted to pH 9.6 with a 5N aqueous sodium hydroxide solution with ice-cooling The organic layer was separated and 30 ml of water was added thereto and the mixture was adjusted to pH 1.5 with 2N hydrochloric acid with ice-cooling. The aqueous layer was separated and 50 ml of chloroform was added. The mixture was adjusted to pH 9.6 with a 5N aqueous sodium hydroxide solution with ice-cooling.

The organic layer was separated and washed with 30 ml of a saturated aqueous sodium chloride solution. The solvent was removed by distillation under reduced pressure. The oily residue thus obtained was dissolved in 50 ml of methanol. Thereto was added 2.0 g of a 28% by weight sodium methoxide solution in methanol. The mixture was stirred in a nitrogen atmosphere at room temperature for 1 hour. 2.6 ml of a 4N hydrochloric acid-ethanol solution was added with ice-cooling. The mixture was stirred at the same temperature for 15 minutes. The solvent was removed by distillation under reduced pressure. The residue thus obtained was purified by a column chromatography (eluant: chloroform:methanol:aqueous ammonia solution=85:15:1) to obtain 3.57 g (yield: 75%) of N-[2-hydroxy-2-(4-hydroxyphenyl)ethyl]-N'-methanesulfonyl-N''-[2-[[5-(methylamino)methyl-2furyl]methylthio]ethyl]guanidine.

This compound showed the same melting point, IR spectrum and NMR spectrum as those of the compound obtained in Example 1 (1).

PREPARATION EXAMPLE 1

There were uniformly mixed 75 g of N-[2-hydroxy-2-(4-hydroxyphenyl)ethyl]-N'-methanesulfonyl-N''-[2-[[5-(methylamino)methyl-2-furyl]methylthio]ethyl]guanidine, 15 g of Avicel PH 102 (a microcrystalline cellulose manufactured by ASAHI CHEMICAL INDUSTRY, CO., LTD.), 29 g of Kollidon CL (a cross-linked polyvinyl pyrrolidone manufactured by BASF), 29 g of Adsolider 101 (anhydrous silicic acid manufactured by Freund IND. CO., LTD.) and 3 g of stearic acid and 1.5 g of magnesium stearate. This mixture was made into slugs according to an ordinary method. The slugs were ground and sieved through a 24-mesh screen. The resulting powder was mixed with 4.48 g of Kollidon CL, 5.76 g of Adsolider 102 (anhydrous silicic acid manufactured by Freund IND. CO., LTD.), 4.9 g of Avicel PH 302 (a microcrystalline cellulose manufactured by ASAHI CHEMICAL INDUSTRY, CO., LTD.) and 2.36 g of magnesium stearate. The mixture was made into tablets each weighing 170 mg.

PREPARATION EXAMPLE 2

10 g of N-[2-hydroxy-2-(4-hydroxyphenyl)ethyl]-N'-methanesulfonyl-N''-[2-[[5-(methylamino)methyl-2-furyl]methylthio]ethyl]guanidine and 5 g of L-asparatic acid were suspended in 200 ml of distilled water for injection. The suspension was adjusted to pH 5.5±0.5 with 1N hydrochloric acid with stirring to form a solution. 25 g of D-mannitol was dissolved therein, and the resulting solution was subjected to sterile filtration using a 0.22 μm filter. The filtrate was filled into vials in an amount of 2 ml per vial. The vials were subjected to lyophilization according to an ordinary method to obtain an injection vial.

What is claimed is:

1. An amine derivative represented by the formula:

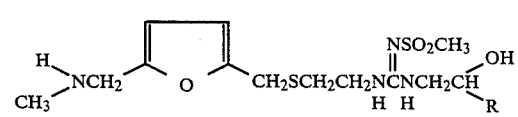

wherein R is a 4-hydroxyphenyl group, a 4-carbamoylphenyl group or a 3-methanesulfonylaminophenyl group, or its salt.

2. An amine derivative or its salt according to claim 1, wherein R is a 4-hydroxyphenyl group.

3. An amine derivative or its salt according to claim 1, wherein R is a 4-carbamoylphenyl group.

4. An amine derivative or its salt according to claim 1, wherein R is a 3-methanesulfonylaminophenyl group.

5. An anti-ulcer composition, comprising an effective amount of an amine derivative represented by the formula:

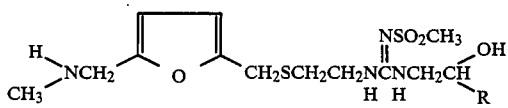

wherein R is a 4-hydroxyphenyl group, a 4-carbamoylphenyl group or a 3-methanesulfonylaminophenyl group or its salt and a pharmaceutically acceptable carrier or diluent.

6. An anti-ulcer composition according to claim 5, wherein R is a 4-hydroxyphenyl group.

7. An anti-ulcer composition according to claim 5, wherein R is a 4-carbamoylphenyl group.

8. An anti-ulcer composition according to claim 5, wherein R is a 3-methanesulfonylaminophenyl group.

9. A method for treating a patient with a peptic ulcer, comprising administering a therapeutically effective amount of an amine derivative represented by the formula:

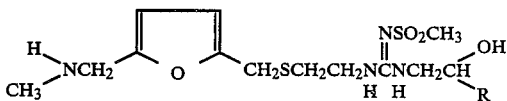

wherein R is a 4-hydroxyphenyl group, a 4-carbamoylphenyl group, or a 3-methanesulfonylaminophenyl group, or its salt.

10. The method according to claim 9, wherein R is a 4-hydroxyphenyl group.

11. The method according to claim 9, wherein R is a 4-carbamoylphenyl group.

12. The method of claim 9, wherein R is a 3-methanesulfonylaminophenyl group.

* * * * *